United States Patent [19]

Flanagan et al.

[11] Patent Number: 5,013,856

[45] Date of Patent: May 7, 1991

[54] 1,5-DIAZIDO-3-NITRAZAPENTANE AND METHOD OF PREPARATION THEREOF

[75] Inventors: Joseph E. Flanagan, Woodland Hills; Edgar R. Wilson, Glendale; Milton B. Frankel, Tarzana, all of Calif.

[73] Assignee: Rockwell International Corporation

[21] Appl. No.: 270,453

[22] Filed: Jun. 4, 1981

[51] Int. Cl.$^5$ ............................................. C07C 247/02
[52] U.S. Cl. ..................................... 552/11; 149/19.1; 149/19.8; 149/92
[58] Field of Search ........................... 260/349; 552/11

[56] References Cited

U.S. PATENT DOCUMENTS

| | | | |
|---|---|---|---|
| 1,620,714 | 3/1927 | Bergeim | 260/349 |
| 1,824,848 | 9/1931 | Turek | 260/349 X |
| 2,286,169 | 6/1942 | Hechenbleikner | 260/349 X |
| 2,769,819 | 11/1956 | Sommers et al. | 260/349 |
| 3,382,256 | 5/1968 | Carabateas | 260/349 |
| 3,873,579 | 3/1979 | Rosher | 260/349 |
| 3,883,374 | 5/1975 | Rosher | 149/20 X |
| 3,883,377 | 5/1975 | Wright | 260/349 X |
| 4,085,123 | 4/1978 | Flanagan et al. | 260/349 |
| 4,141,910 | 2/1979 | Flanagan et al. | 260/349 |
| 4,450,110 | 5/1984 | Simmons et al. | 552/11 |

OTHER PUBLICATIONS

Chute et al., "Catalyzed Nitration of Amines I. Dinitroxydiethylnitramine", *Can. J. Res.*, 26, Sec. B, 89–103 (1948).

*Chemical Abstracts*, vol. 81 (1974), p. 440, No. 119448q. Gidaspov et al., "Kinetics of Azidation of Ethylene Chlorohydrin Nitrate in Certain Solvents", Isv. Vyssh. Uchebn. Zaved., Khim Khim. Tekhnol. (1974), 17(7), 1030–4 (Russ.).

*Primary Examiner*—Richard D. Lovering

[57] ABSTRACT

1,5-Diazido-3-Nitrazapentane is disclosed as an energetic plasticizer, together with a method for producing same.

6 Claims, No Drawings

1,5-DIAZIDO-3-NITRAZAPENTANE AND METHOD OF PREPARATION THEREOF

BACKGROUND OF THE INVENTION

1. Field of the Invention

This invention relates to the field of solid propellant formulations and more specifically to energetic plasticizers for use in solid propellant compositions.

2. Description of the Prior Art

This invention generally relates to the preparation and use of 1,5-diazido-3-nitrazapentane. Solid propellants, gun propellants, and explosives are generally composed of oxidizers, binders, plasticizers, and sometimes a fuel. The oxidizers such as ammonium perchlorate and HMX are well known to the art. Hydrocarbon binders and inert plasticizers such as phthalates and triacetin are generally used. Finally, a fuel such as aluminum may be added. Recently, attempts have been made to replace the inert plasticizers with an energetic material so as to increase the specific impulse and burning rate of the propellant.

Recent work has indicated that azidomethyl nitramines

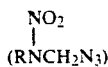

constitute an attractive class of energetic plasticizers, U.S. Pat. Nos. 3,873,579 to Rosher and 4,085,123 to Flanagan et al. The process for preparing this class of compounds is based on first preparing a primary nitramine

reacting it with formaldehyde and anhydrous HCl to form the chloromethylated product

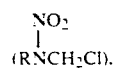

and finally treating this product with an ionic azide to form the azidomethyl nitramine

The overall process is shown below:

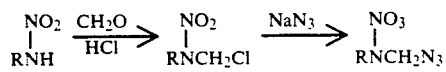

This process has two severe limitations. First, it requires a primary nitramine as the starting material. The synthesis of primary nitramines, themselves, requires a multi-step process. Furthermore, they are hazardous to handle because of the mobility of the acidic hydrogen atom. Secondly, this process is based on the preparation of a chloromethylated intermediate. Thus, it is only possible to produce an azidomethyl nitramine. Obviously, it would be of interest to have a method for preparing higher homologs such as azidoethyl nitramines, which would have improved physical properties, particularly sensitivity.

SUMMARY OF THE INVENTION

Accordingly, there is provided by the present invention an energetic plasticizer denoted as 1,5-diazido-3-nitrazapentane. The subject novel energetic plasticizer is prepared by treating 1,5-dinitrato-3-nitrazapentane with an ionic azide such as sodium azide in an aprotic solvent such as dimethylformamide or dimethylsulfoxide.

OBJECTS OF THE INVENTION

Therefore, one object of this invention is to provide materials which can successfully replace all or part of inert plasticizers in solid propellants, gun propellants, or explosives.

Another object of this invention is to effect an increase in both specific impulse and burning rate of solid propellants.

A still further object of this invention is to provide 1,5-diazido-3-nitrazapentane.

A further object of this invention is to provide a convenient method for the production of 1,5-diazido-3-nitrazapentane from readily available starting materials.

Other objects, advantages and novel features of the present invention will become apparent from the following detailed description of the invention.

DESCRIPTION OF THE PREFERRED EMBODIMENTS

The compound of the present invention is readily prepared by the nitration of diethanolamine to 1,5-dinitrato-3-nitrazapentane according to the well established procedure. Chute, W. J., K. G. Herring, L. E. Toombs, and G. F. Wright, *Can. J. Res.*, 26, Sec. B, 89 (1948), and then treating the nitramino alkyl nitrate with an ionic azide such as $NaN_3$, $KN_3$, $LiN_3$, to give the desired 1,5-diazido-3-nitrazapentane:

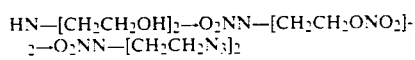

Due to its ready availability, the most preferred ionic azide is the sodium azide, $NaN_3$.

The preferred and most expeditious means for carrying out the above reaction is in a dipolar aprotic solvent such as dimethylformamide or dimethylsulfoxide. These solvents are used routinely as a media for azide substitution reactions. Although the reaction temperature can range from about 25° to about 95° C., the preferred range is from about 50° to about 90° C.

The above reaction can also be carried out at the same temperature range in aqueous medium using a phase transfer catalyst such a methyl-tricaprylyl ammonium chloride. The compositions contemplated by this invention include the known compositions of gun propellants and solid propellants where some or all of the inert plasticizer has been replaced by the compound of this invention.

The simplest composition contemplated by this invention is merely a mixture of 1,5-diazido-3-nitrazapentane and nitrocellulose. A composition such as this when used as a gun propellant serves to increase impetus without increasing the flame temperature significantly by virtue of the fact that this composition produces more gas per unit weight on decomposition than a typical double-base composition of nitrocellulose-nitroglycerin propellant.

The specific impulse of typical solid propellant compositions can be increased by replacing inert plasticizers such as triacetin with the compound of this invention.

The general nature of the invention having been set forth, the following example is presented as a specific illustration thereof. It will be understood that the invention is not limited to this specific example but is susceptible to various modifications that will be recognized by one of ordinary skill in the art.

EXAMPLE 1

Preparation of 1,5-Diazido-3-Nitrazapentane

A mixture of 12 g (0.05 m) of 1,5-dinitrato-3-nitrazapentane, 7.2 g (0.11 m) of sodium azide, and 24 ml of dimethylformamide was heated at 85°–90° C. for 27 hours. The reaction mixture was cooled and poured into 100 ml of water.

Methylene chloride (10 ml) was added, the mixture stirred, and the methylene chloride layer separated. The aqueous layer was extracted with $2 \times 10$ ml of methylene chloride. The extracts were combined, washed with $6 \times 100$ ml of water, dried over anhydrous sodium sulfate and concentrated to give 6.3 g (63%) of light yellow oil, $n^{25}D$ 1.5259. Purity by G.C. was 100%. Elemental and infrared analysis confirmed the product to be 1,5-diazido-3-nitrazapentane.

The infrared spectrum showed the strong absorptions for azide at 4.8 u and nitraza at 6.6 u.

| Elemental Analyses | | | |
|---|---|---|---|
| | C | H | N |
| Calculated for $C_4H_8N_8O_2$: | 24.00 | 4.03 | 55.98 |
| Found: | 23.98 | 4.01 | 55.94 |

Obviously, many modifications and variations of the present invention are possible in light of the above teachings. It is therefore to be understood that, within the scope of the appended claims, the invention may be practiced otherwise than as specifically described.

What is claimed and desired to be secured by Letters Patent of the United States is:

1. A composition of matter comprising 1,5-diazido-3-nitrazapentane.

2. The azido nitramine composition 1,5-diazido-3-nitrazapentane.

3. A method of preparing 1,5-diazido-3-nitrazapentane, comprising the steps of:
combining 1,5-dinitrato-3-nitrazapentane with an ionic azide selected from the group consisting of $NaN_3$, $KN_3$, and $LiN_3$, in a dipolar aprotic solvent selected from the group consisting of dimethylformamide and dimethylsulfoxide to form a reaction system;
heating said reaction system to a temperature ranging from about 25° C. to about 95° C.;
maintaining said reaction system within said temperature range;
reacting said 1,5-dinitrato-3-nitrazapentane with said ionic azide; and
separating said 1,5-diazido-3-nitrazapentane from said reaction by-products.

4. The method of claim 3 wherein said ionic azide is sodium azide, $NaN_3$.

5. The method of claim 3 wherein said separation comprises the steps of:
admixing said reaction system with water to form an aqueous solution;
adding a halogenated hydrocarbon to said aqueous solution to dissolve said 1,5-diazido-3-nitrazapentane product and form a product-rich layer;
extracting said product-rich layer;
water washing said product-rich layer to remove any remaining by-product;
drying said product-rich layer; and
concentrating said product-rich layer to yield said 1,5-diazido-3-nitrazapentane.

6. The method of claim 5 wherein said halogenated hydrocarbon is methylene chloride.

* * * * *